(12) United States Patent
Elgue et al.

(10) Patent No.: US 8,065,038 B2
(45) Date of Patent: Nov. 22, 2011

(54) OPTIMIZING A CHEMICAL REACTION IN A PLATE-TYPE OPEN REACTOR

(75) Inventors: Sébastien Elgue, Baziege (FR); Fabrice Chopard, Saint Martin d'Heres (FR); Michel Roger Cabassud, Saint Orens de Gameville (FR); Patrick Alain Cognet, Toulouse (FR); Laurent Emile Georges Prat, Toulouse (FR); Christophe Jacques Jean Gourdon, Toulouse (FR)

(73) Assignee: Alfa Laval Vicarb, Fontanil Cornillon (FR)

( * ) Notice: Subject to any disclaimer, the term of this patent is extended or adjusted under 35 U.S.C. 154(b) by 739 days.

(21) Appl. No.: 11/773,667

(22) Filed: Jul. 5, 2007
(Under 37 CFR 1.47)

(65) Prior Publication Data
US 2008/0140376 A1    Jun. 12, 2008

Related U.S. Application Data

(63) Continuation of application No. PCT/FR2006/000049, filed on Jan. 10, 2006.

(30) Foreign Application Priority Data

Jan. 14, 2005   (FR) .................................... 05 00424

(51) Int. Cl.
 *G06G 7/58* (2006.01)
 *G06F 7/60* (2006.01)
 *G05B 21/00* (2006.01)
(52) U.S. Cl. ............ 700/266; 700/268; 702/22; 703/2; 703/12

(58) Field of Classification Search .................. 700/268; 702/22; 703/2, 12
See application file for complete search history.

(56) References Cited

U.S. PATENT DOCUMENTS
2004/0109798 A1 *   6/2004   Chopard et al. .............. 422/198

FOREIGN PATENT DOCUMENTS
WO         WO 02/085511  A1     10/2002

OTHER PUBLICATIONS
French Search Report for Application No. FR 05 00424; Search completed on Oct. 13, 2005.

(Continued)

*Primary Examiner* — Lyle Alexander
*Assistant Examiner* — Dean Kwak
(74) *Attorney, Agent, or Firm* — Alston & Bird LLP

(57) ABSTRACT

A method of optimizing a chemical reaction in a plate-type open reactor, the method consisting in:
- establishing a dynamic model of the reactor for a given reaction on the basis of a model of the reactor and its heat exchanges;
- applying an integration software tool to the dynamic model in order to solve the above-mentioned equations;
- determining and optimizing a set of dimension and/or operation parameters of the reactor on the basis of evaluating targets to be achieved, constraints to be complied with, and variable data for the reactor and/or the reaction;
- building a plate reactor of the said type accordingly to the set of optimized parameters; and
- doing measurements of physical parameters during the execution of said reaction in the built reactor, for validating its operation.

21 Claims, 9 Drawing Sheets

OTHER PUBLICATIONS

Calvet, J.P., et al; Modelling, optimisation and control of a continuous multistage reactor for an industrial reactive system; Journal A, Soft Vision, Brussels, BE, vol. 35, No. 1, Apr. 1, 1994, pp. 5-15.

Andersson, R., et al.; Development of a multi-scale simulation method for design of novel multiphase reactors; Chemical Engineering Science, Oxford, GB, vol. 59, No. 22-23, Nov. 2004, pp. 4911-4917.

Zhang, J., et al; Design and optimisation of batch and semi-batch reactors; Chemical Engineering Science, Oxford, GB, vol. 59, No. 2, Jan. 2004, pp. 459-478.

* cited by examiner

OPTIMIZING A CHEMICAL REACTION IN A PLATE-TYPE OPEN REACTOR

CROSS REFERENCE TO RELATED APPLICATIONS

This application is a Continuation Application of International Application No. PCT/FR2006/000049, filed Jan. 10, 2006, which claims priority from French patent Application No. 0500424 filed Jan. 14, 2005.

FIELD AND BACKGROUND OF THE INVENTION

The present invention relates to a method of optimizing a chemical reaction in a plate-type open reactor constituted by a stack of plates defining between them at least one block having a reaction chamber and two side chambers for circulating a heat-exchange utility fluid.

Attempts are being made at present to optimize the running and to improve the yield of chemical reactions in general, which reactions are usually implemented in batch type reactors, i.e. reactors that operate discontinuously, comprising vessels in which determined quantities of reagents are placed and mixed together, and subsequently subjected to environmental conditions (pressure, temperature, pH, etc.) optimized for promoting the reactions.

A major drawback of such reactors is the difficulty of removing the heat produced by a reaction, which puts constraints on controlling and optimizing the reaction.

SUMMARY OF THE INVENTION

A particular object of the present invention is to provide a simple and effective solution for controlling and optimizing chemical reactions by optimizing a reactor of the open type, which solution does not present the above-mentioned drawbacks of discontinuous reactors or batch type reactors.

To this end, the invention provides a method of optimizing a chemical reaction in a reactor, the method being characterized in that it consists in:
  using an open reactor constituted by a stack of plates defining between them at least one block having a reaction chamber formed between two heat exchange side chambers for circulating a heat exchange utility fluid, means for feeding the reaction chamber with a continuous flow of one or more reagents, and means for feeding the two side chambers with a continuous flow of utility fluid;
  establishing a dynamic model of the reactor for a given reaction on the basis of a model of the reaction chamber and of the heat exchanges between said reaction chamber and the side chambers for circulating utility fluid, the dynamic model comprising mass balance and energy balance equations, and constraint equations;
  applying an integration software tool to the dynamic model to solve the above equations;
  determining and optimizing a set of dimension and/or operation parameters of the reactor on the basis of evaluating targets to be achieved, constraints to be complied with, and variable data for the reactor and/or the reaction;
  building a plate reactor of the said type accordingly to the set of optimized parameters; and
  doing measurements of physical parameters such as the temperature and the pressure during the execution of said reaction in the built reactor, for validating its operation.

Using a continuous or open reactor comprising a stack of plates defining at least one reaction chamber between two utility fluid circulation chambers makes it possible to solve the problems of heat dissipation that are observed in discontinuous or closed reactors of the batch type, by appropriately selecting the temperatures and flow rates of the utility fluid(s) circulating on either side of the reaction chamber, and also by selecting the flow directions of these fluids (co-current, counter-current, or crossed-currents) relative to the flow direction of the reaction fluid in the reaction chamber.

This also makes it possible to optimize the dimensions or the optimum configuration of the reactor and to optimize the operation or the operating conditions of the reactor by providing control parameters for the chemical reaction, and by describing accurately the temperature distribution within the reactor.

Accurately determining the way in which temperatures vary within the reactor, which constitutes the essential difference between the invention and prior methods of optimizing reactions in discontinuous reactors, is made possible by dynamic modeling of the reactor for the reaction in question, and by optimizing a set of dimension and/or operation parameters of the reactor as a function of the targets to be achieved and of the constraints to be complied with.

A plate reactor of the said type is then built accordingly to the set of dimension and/or operation parameters beforehand optimized, the chemical reaction is executed in this reactor and experimental measurements of physical parameters are done for validating the chemical reaction optimization.

The method of the invention may also consist in, after the building of the reactor:
  establishing a new dynamic model of the reactor on the basis of the built reactor;
  applying the integration software tool to this new dynamic model to solve the above equations;
  optimizing again the said set of dimension and/or operation parameters of the reactor; and
  modifying if necessary the said built reactor, accordingly to the new optimized set of parameters.

The dynamic model of the reactor comprises mass and energy balance equations and constraint equations, which are characteristics of the reactor and of the chemical reaction.

According to another characteristic of the invention, the model of the reaction chamber includes subdividing the chamber into a series of successive individual cells, each containing a thoroughly stirred fluid medium. The utility fluid circulation chambers are likewise modeled by being subdivided into individual cells of number equal to the number of individual cells in the reaction chamber.

The modeling of heat exchanges also takes account of the flow direction of the fluid in each individual cell of the reaction chamber relative to the flow direction (co-current, counter-current, crossed-currents) of the utility fluid(s) in the individual cells corresponding to the side chambers situated on either side of said individual cell of the reaction chamber. The model also comprises heat balance equations relating to the reaction fluid, to the plates defining the side heat exchange chambers, and to the utility fluids circulating in the side chambers, and mass balance equations for the reaction medium and for the utility fluids in the individual cells of the various chambers.

Each reaction chamber is connected to inlet zones and outlet zones which are associated with an individual cell of the reaction chamber and which are, for example, connection elements between the reagent feed means and a reaction chamber feed point, and connection elements between a reaction chamber outlet point and means for collecting the product of the reaction. When two reaction chambers are connected together in series, the outlet element of the first chamber coincides with the inlet element of the second chamber.

Advantageously, the dynamic model of the reactor includes a model of the inlet and outlet zones of the reactor, of the inlet and outlet zones of each reaction chamber, and of transition zones between the various blocks of the reactor.

The dynamic model also makes it possible to have a feed point for each individual cell of the reaction chamber.

The integration software tool applied to the system of equations constituting the dynamic model of the reactor serves to solve those equations and to simulate the behavior of the reactor, known as the "reactor state", for the chemical reaction under study.

For given targets and constraints, the dimension parameters of the reactor are determined and optimized both by adjusting variable characteristics of the reactor, which variable characteristics comprise the number of feed points in the reaction chamber, the flow direction(s) of the utility fluid(s) relative to the reaction medium, the nature and the distribution of the utility fluid(s), the total volume of the reaction chamber, and/or the volumes of the side chambers for utility fluid circulation, and for given targets and constraints, the operation parameters of the reactor are determined and optimized both by adjusting variable reaction data or operating parameters comprising temperatures, pressures, compositions, and/or flow rates of the reaction medium and of the utility fluid(s).

The method consists, for example, in adjusting the feed rates of one or more reagents to the various individual cells in order to obtain a better yield for the reaction, and in defining limit values for the operating parameters in order to satisfy safety and/or environmental constraints.

For a chemical reaction in a homogeneous medium, the dynamic model of the reactor comprises a dynamic model of the reaction chamber made up of equations for mass balance, energy balance, pressure balance, and volume constraints. These equations serve to define the state of and the variations in the fluid medium in each individual cell.

To do this, it is considered that in the individual cells of the reaction chamber having thoroughly stirred content, the characteristic magnitudes (temperature, pressure, flow rate, composition, etc.), the physical properties (density, viscosity, etc.), and the physico-chemical phenomena (reaction, transfer of material, etc.), are uniform within each cell, and that the physical properties of the utility fluids are uniform and constant for a given temperature.

For a chemical reaction in a two-phase medium (liquid-liquid or liquid-gas), where the reaction medium is a mixture of a continuous phase and a dispersed phase, and for a reaction medium that is a mixture of two miscible liquids, the state of and the variation in the reaction medium are defined in each individual cell from equations for estimating the density, the specific heat, the thermal conductivity, and the viscosity of the reaction medium, and from equations for the mass balance, the energy balance, the pressure balance, and the volume constraints.

It is considered that in the individual cells of the reaction chamber having content that is thoroughly stirred, the characteristic magnitudes (temperature, pressure, flow rate, composition), the physical properties (density, viscosity, etc.), and the physico-chemical phenomena (reaction, transfer of material, etc.), are uniform within each cell, the temperatures and the pressures of the phases are identical, and the reactor medium is taken to be a pseudo-homogeneous medium and the physical properties of the two phases are determined by association relationships enabling the physical properties of the medium to be associated with the properties of each of the phases and also with their proportions, the distribution of the phases being assumed to be uniform in each individual cell.

It is also possible for two-phase equilibrium rules to be applied to the phase mixture as a function of the size of the droplets of the dispersed phase, of the thermodynamic properties of the phases that are present, and/or of the flow conditions.

The Sauter diameter makes it possible to determine the size of the droplets of the dispersed phase. Variations in the size of the droplets in the dispersed phase can also be tracked in the various individual cells of the reaction chamber.

Other models can add to and refine the dynamic model of the reactor, such as:
- modeling the hydrodynamic behavior of the reactor on the basis of experimental studies of the resident time distribution of the fluids in the various portions of the reactor, and enabling the number of individual cells having thoroughly stirred content to be defined;
- a reaction model based on equations for rate of reaction, rate of production of reaction constituents, and rate of heat generation, in each individual cell of the reaction chamber(s);
- a matter transfer model in a reaction in a two-phase medium between the two phases of the reaction medium, on the basis of the physical properties of the two-phase medium and on the basis of the size of the droplets of the dispersed phase;
- a heat transfer model based on definitions of heat transfer coefficients between the plates defining the side chambers and the fluids circulating in the reaction chamber and in the side chambers, and on the basis of estimated film coefficients for the reaction fluid and for the utility fluid; and
- a model of reaction fluid pressure drops in the reactor, based on experimental measurements.

The method may also include estimating the physical properties of the components of the reactor and of the reaction and utility fluids.

The method of the present invention presents the advantage of predicting the behavior of a plate reactor for given operating conditions, and it also makes it possible to define the optimum configuration or dimensioning and the optimum operating conditions or operation of the reactor for a given reaction or set of reactions. The method also makes it possible to describe variations in said behavior over time, with it being possible to represent such variation in numerous ways in terms of optimizing control of the reactor, studying safety, and managing non-production transient periods.

BRIEF DESCRIPTION OF THE DRAWINGS

Other advantages and characteristics of the invention will appear on reading the following description made by way of non-limiting example and with reference to the accompanying drawings, in which.

MORE DETAILED DESCRIPTION

Figure 1:
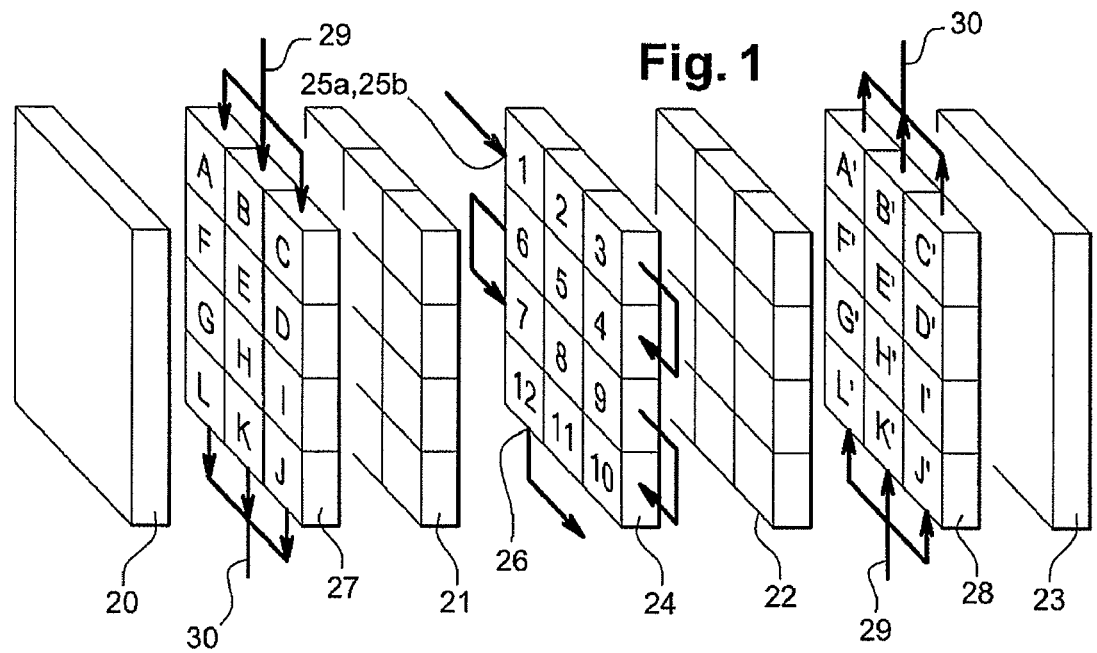
FIG. 1 is a diagrammatic exploded perspective view of an open plate-type reactor used in the method of the invention.

Reference is made initially to FIG. 1 which is a diagram of an open or continuous reactor comprising a stack of plates 20, 21, 22, 23 which define parallel chambers between one another. The plates 21 and 22 are referred to as "transition" plates and they define between them a reaction chamber 24 having a reagent feed point 25a and one or more feed points 25b for one or more other reagents, and an outlet point 26 for the product(s) of the reaction. The plates 20 and 23 are adiabatic plates and they co-operate with the plates 21 and 22 to define a left side chamber 27 and a right side chamber 28 for circulating a heat exchange utility fluid, each side chamber 27, 28 having an inlet 29 and an outlet 30 for the utility fluid.

The utility fluid which circulates in the left side chamber 27 may be identical to or different from that which circulates in the right side chamber 28, and the utility fluid that is commonly used is water or ethylene glycol.

The stack of plates 20, 21, 22, 23 forms a reaction block, and the plates 20 and 23 serve to isolate it thermally from the outside environment or from one or more reaction blocks connected in series therewith.

Figure 2:
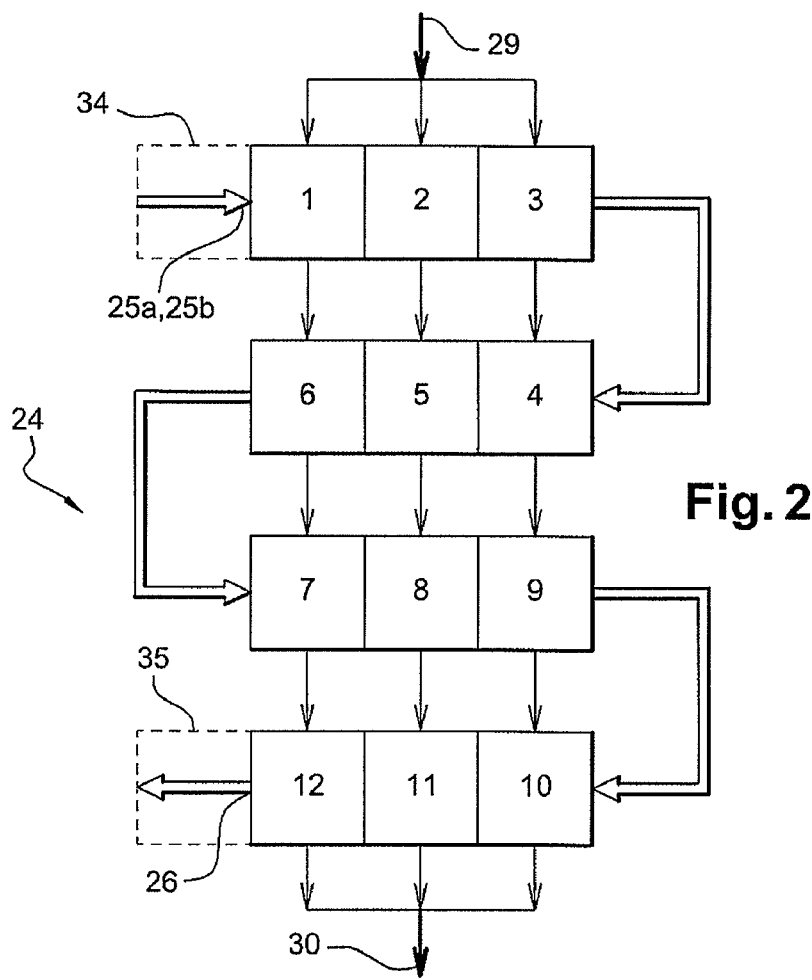
FIG. 2 is a diagrammatic view of the reaction chamber of the FIG. 1 reactor subdivided into individual cells.

The chambers 24, 27, and 28 are generally fitted with means defining fluid flow passages inside said chambers. For example, the reaction chamber 24 includes inserts forming a baffle constraining the reaction medium to follow a zigzag path inside the reaction chamber 29, as shown in FIGS. 1 and 2.

The chambers 24, 27, and 28 are fed continuously by suitable means (not shown).

Under optimum operating conditions, the overall heat transfer coefficient of a plate reactor may lie in the range 2000 watts per square meter per Kelvin ($W.m^{-2}.K^{-1}$) to 5000 $W.m^{-2}.K^{-1}$. The temperature in the reaction chamber 24 is controlled, for example, by suitably selecting the temperature and/or the flow rate of the utility fluid(s) circulating on either side of the reaction chamber 24, and also by appropriately selecting the composition, the temperature, and/or the flow rate of the reaction medium in the reaction chamber, and/or by appropriately selecting the flow direction of the utility fluid in each side chamber relative to that of the reaction medium in the reaction chamber. A utility fluid flows as a co-current if it flows in the two side chambers 27 and 28 in the same direction as the reaction medium flows in the reaction chamber 24, as a counter-current if it flows in the opposite direction, and as crossed-currents if it flows in one side chamber in the same direction as the reaction medium and in the opposite direction in the other side chamber, as shown in FIG. 1. In this example, the reaction medium and the utility fluid cross because the reaction medium is flowing horizontally following a zigzag path and the utility fluid is flowing vertically, but any other flow configuration could be adopted, such as a parallel configuration.

An essential characteristic of the method of the invention consists in establishing a dynamic model of the reactor for a given reaction.

The model comprises subdividing the reaction chamber into individual cells each of which is thoroughly stirred, by means of experimental investigation of resident time distribution, thereby making it possible to analyze the flow and discover dead volumes and preferred passages, and enabling the mixture in the reaction chamber 24 to be characterized.

Experimental analysis of the resident time distribution makes it possible to characterize it in terms of mean resident time ($\bar{t}$) and of variance ($\sigma^2$). On the basis of these characteristics, it is possible to estimate the number of individual cells needed in order to be representative of the degree of mixing and the hydrodynamics of the real reactor. By way of example, this number is calculated using the following formula:

$$N = \frac{\bar{t}^2}{\sigma^2}$$

In practice, this number depends in particular on the feed rate of the reaction chamber 24 and on the viscosity of the reaction medium. The number of individual cells for a plate reactor comprising three reaction blocks is, for example, 70 for a reaction medium made up solely of water fed at a rate of 25 liters per hour ($L.^{-1}$), 100 for water fed at 50 $L.h^{-1}$, 130 for water fed at 80 $L.h^{-1}$, and 25 for a reaction medium made up of ethylene glycol fed at a rate of 50 $L.h^{-1}$.

In the example of FIGS. 1 and 2, the reaction chamber has twelve individual cells. These twelve individual cells are numbered 1 to 12 following the horizontal zigzag flow order of the reaction medium through the reaction chamber 24 from the feed point(s) 25a, 25b to the outlet point 26 of said chamber 24. This flow is imposed by the above-mentioned insert present in the reaction chamber 24.

The twelve cells make up four rows of three cells each. A reagent is introduced into the reaction chamber 24 from the feed point 25a in cell 1. The reaction medium passes horizontally from cell 1 to cell 2 and then to cell 3, it leaves cell 3 and penetrates into cell 4 situated vertically beneath it, and then passes horizontally into cells 5 and 6. The reaction medium leaves the cell 6 and penetrates into cell 7 situated vertically beneath it, and then passes horizontally into cells 8 and 9. Finally, the reaction medium leaves the cell 9 and penetrates into cell 10 situated vertically beneath it, and then passes horizontally into cells 11 and 12 in order to leave the reaction chamber 24 via the point 26. Other feed points 25b for one or more other reagents can also be provided in the first cell or in individual cells other than the first.

In a variant, the reaction medium can flow in the reaction chamber 24 in parallel relative to the utility fluid flowing in the side chambers 27 and 28.

Similarly, the side chambers 27 and 28 are subdivided into individual cells for utility fluid flow, so that each individual reactor cell is situated between two individual utility fluid flow cells.

In FIG. 1, the left and right side chambers 27 and 28 comprise respective series A, B, C, D, E, F, G, H, I, J, K, L, and A', B', C', D', E', F', G', H', I', J', K', L' of individual utility fluid flow cells. The alphabetical order of the cell letters matches the order of increasing number for the individual reaction cells, and does not match the flow of the utility fluid which is downwards in the left-hand chamber 27 and upwards in the right-hand chamber 28.

By subdividing the reactor chamber 24 into individual cells, it is possible for the reaction medium flowing in each individual reaction cell to determine the thermal influence of the utility fluid flowing in the two corresponding side individual cells, acting through the two transition plates 21 and 22 defining the reaction chamber 24. For example, heat can be exchanged between individual utility fluid flow cell E and the individual reaction cell 5 through the plate 21, and between individual utility fluid flow cell E' and the individual reaction cell 5 through the plate 22.

In the embodiment shown in FIG. 1, the thermal characteristics of the cell 5 are determined by those of the cell situated immediately ahead of it in the fluid flow direction of the reaction medium, i.e. the cell 4. Similarly, the thermal characteristics of the cells E and E' are determined respectively by the cells B and H' situated ahead of E and E' respectively in the utility fluid flow direction.

The individual reaction cells are considered as being continuously stirred reactors, thus making it possible to generalize the equations for the characteristics and balances of the reactor and of the chemical reaction in the mathematical model using a number of equations which is a function of the number of individual reaction cells, where this number is given by the following expression:

$n$=[No. of cells]×(No. of equations per cell)

The number of equations in the mathematical model is also a function of the number of zones used in the utility fluid flow chambers. The term "utility zone" is used to mean a portion of the utility fluid flow chamber which has its own utility fluid feed and outlet points. A utility fluid flow chamber having three utility zones thus presents three feed points and three outlet points for the utility fluid. The number of equations in the mathematical model is then given by the following expression:

$n$=[No. of cells]×(No. of equations per cell)+(No. of equations per zone)[No. of utility zones]

Depending on the model under consideration, i.e. for a homogeneous medium or a two-phase medium, the number of equations is not the same, with the total number of equations of the model being defined by the following equations:
homogeneous model:

$n$=[($n_{cell/block}$+3)×$n_{block}$+1]×(16+$n_{cons}$)+ 3×$n_{zone/block}$×$n_{block}$;

two-phase model;

$n$[($n_{cell/block}$+3)×$n_{block}$+1]×(21+2×$n_{cons}$)+ 3×$n_{zone/block}$×$n_{block}$;

in which $n_{cons}$ is the number of constituents of the chemical reaction, $n_{block}$ is the number of reaction blocks, $n_{zone/block}$ is the number of utility zones per reaction block, and $n_{cell/block}$ is the number of individual cells per reaction block.

For a chemical reaction in a homogeneous or single-phase medium, the characteristic equations are as follows, for example:
for each individual cell of the reaction chamber: an overall mass balance, component mass balances, an energy balance, a pressure balance, a volume model, a molar enthalpy model, a volume constraint, a molar volume model, a heat balance for the thermal environment, heat balances for the transition plates, heat balances for the utility fluids, heat balances for the adiabatic plates, and mass balances for the utility fluids; and
for each utility zone in the utility fluid flow: utility fluid temperature constraints and a utility fluid flow rate constraint.

For a chemical reaction in a two-phase or heterogeneous medium, the characteristic equations are as follows, for example:
for each individual cell of the reaction chamber: overall mass balance for the continuous phase and for the dispersed phase, component mass balance for the continuous phase and for the dispersed phase, an energy balance, a pressure balance, volume models for the continuous phase and for the dispersed phase, molar enthalpy models for the continuous phase and for the dispersed phase, molar volume models for the continuous phase and for the dispersed phase, volume constraints for the dispersed phase and for the continuous phase, a heat balance for the thermal environment, heat balances for the transition plates, heat balances for the utility fluids, heat balances for the adiabatic plates, and mass balances for the utility fluid; and
for each utility zone in the utility fluid flow: utility fluid temperature constraints and a utility fluid flow rate constraint.

Figure 3:
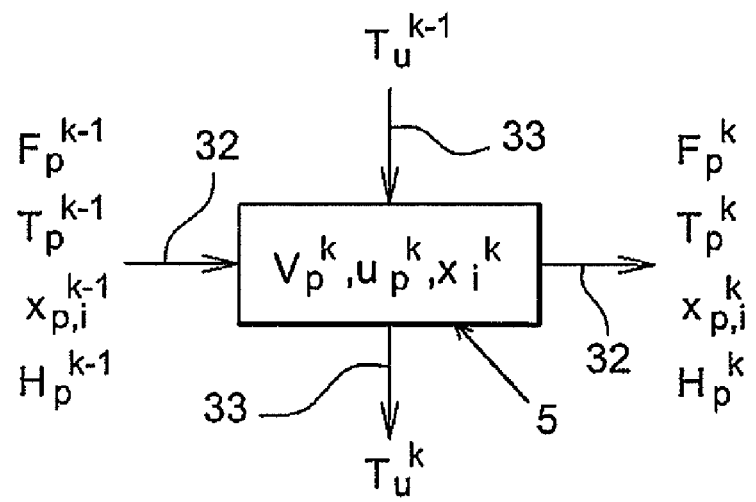
FIG. 3 is a diagrammatic view of an individual cell of the FIG. 2 reaction chamber.

The dynamic reactor model of the invention is drawn up on the basis of a dynamic model of the reaction chamber and a dynamic model for heat exchanges, each dynamic model comprising equations relating to an individual reaction cell 5 represented diagrammatically in FIG. 3 by a rectangle.

Arrows 32 and 33 represent respectively the flow direction of the reaction medium in the individual cell 5 of the reaction chamber 24 and of the utility fluid in the individual side cells E and E' of the side chambers 27 and 28, the utility fluid flow direction in the two chambers 27 and 28 in this example being a co-current flow relative to the flow of the reaction medium in the reaction chamber 24, contrary to that which is shown in FIG. 1.

The indices p and u are used respectively to define the reaction medium and the utility fluid. $F_p$ represents the molar flow rate of the reaction medium in an individual cell and is given in moles per second (mol.s$^{-1}$), $T_p$ and $T_u$ are respectively the temperature of the reaction medium and of the utility fluid in their individual cells expressed in ° K, $H_p$ is the molar enthalpy of the reaction medium in an individual cell expressed in joules per mole (J.mol$^{-1}$), $V_p$ is the volume of an individual reaction chamber expressed in cubic meters (m$^3$), $u_p$ is the number of moles in the reaction medium in an individual cell, and $x_p$ is the molar fraction of a reagent or a constituent (i) in an individual cell, the superscripts k-1 and k indicating the number of the individual reaction cell (1 to 12 in the embodiment of a reaction chamber 24 shown in FIGS. 1 and 2) or the letter of the individual utility fluid flow cell (A to L and A' to L' for the left and right chambers 27 and 28 in FIG. 1).

If it is assumed that the individual cells of the reaction chamber 24 have content that is thoroughly stirred, then the chemical reaction takes place in a homogeneous single-phase liquid medium to which Arrhenius' equation can be applied, and the dynamic model of the reaction chamber comprises the following equations, for example:
the overall mass balance for the reaction medium in an individual cell (in mol.s$^{-1}$):

$$\frac{du_p^k}{dt} = F_p^{f,k} + F_p^{k-1} - F_p^k + \Delta n_p^k \times V_p^k$$

with $$\Delta n_p = \sum_i \Delta n_{p,i}, \; \Delta n_{p,i} = \sum_j \alpha_{i,j} r_j \text{ and}$$

-continued $$r_j = k_j^0 \exp\left(\frac{E_j^a}{RT^k}\right)\prod_i (C_{p,i}^k)^{\beta_{i,j}};$$

the component mass balance for the constituents (i) of the reaction medium in an individual cell (in mol.s$^{-1}$):

$$\frac{d(u_p^k \times x_{p,i}^k)}{dt} = F_p^{f,k} x_{p,i}^{f,k} + F_p^{k-1} x_{p,i}^{k-1} - F_p^k x_{p,i}^k + \Delta n_{p,i}^k \times V_p^k;$$

the pressure balance equation for the reaction medium in an individual cell (in pascals (Pa)):

$$P_p^k = P_p^{k-1} - \Delta P_p^k;$$

the volume model equation for the reaction medium in an individual cell (in m$^3$):

$$V_p^k - mV_p^k = 0 \text{ with } mV_p^k = u_p^k \times V_p^{ml,k};$$

the molar enthalpy equation of the reaction medium in an individual cell (in J.mol$^{-1}$):

$$H_p^k - mH_p^k = 0;$$

the volume constraint or molar flow rate equation for the reaction medium in an individual cell (in m$^3$ or mol.s$^{-1}$):

$$F_p^k = 0$$

during the stage in which all of the individual reaction cells are being filled, and then:

$$u_p^k - \frac{V^{cell}}{V_p^{ml,k}} = 0 \Leftrightarrow V_p^k = V^{cell}$$

once the cells have been filled;
in which F$^f$ is the feed rate in mol.s$^{-1}$, Δn represents production speed in moles per cubic meter per second (mol.m$^{-3}$.s$^{-1}$), α is the stoichiometric coefficient, r is the reaction rate in mol.m$^{-3}$.s$^{-1}$, k° is the pre-exponential factor, E$^a$ is the activation energy in J.mol$^{-1}$, R is the ideal gas constant, C is the reagent concentration in mol.m$^{-3}$, V is volume in m$^3$, mV and mH respectively the model of module and the model of enthalpy (m$^3$ and J.mol$^{-1}$), V$^{m1}$ is the molar volume in cubic meters per mole (m$^3$.mol$^{-1}$), the superscript "cell" designates the physical cell, the superscript β is the reaction order, the subscript j is the number of the reaction, the subscript i is the constituent considered, t is time in s, T is temperature en ° K, P is pressure, and ΔP is pressure drop in pascals (Pa) which is defined by the following equation:

$$\Delta P = \frac{4fL}{d_h}\frac{1}{2}\rho v^2;$$

where the Fanning or friction factor f is given by f=5.0464 Re$^{-0.5328}$ for a flow of the reaction medium through the individual reaction cell that is laminar (Reynolds number Re<2200), or f=2.17347 Re$^{-0.42316}$ for a turbulence flow (Re>2200);
L is the length of the path followed by the reaction medium through the reaction chamber 24 in meters (m), ρ is the density of the reaction medium in kilograms per cubic meter (kg.m$^{-3}$), v is the speed of the reaction medium in meters per second (m.s$^{-1}$), and d$_h$ is the equivalent hydraulic diameter of an individual reaction cell in meters (m).

If it assumed that the plate reactor is constituted by a succession of continuous stirred reactors and that the physical properties of the utility fluid are constant and homogeneous for a given temperature, the dynamic model of the utility fluid comprises the following equations, for example:
the continuity equation for the utility fluid flow (in cubic meters per second (m$^3$.s$^{-1}$))

$$F_u^{in} = F_u^{out}$$

the continuity equation for the temperature of the utility fluid (in kelvins (K)):

$$T_u^{out} = \frac{\sum_{i=nc-ncr+1}^{nc} T_u^i}{ncr}$$

where the superscripts "in" and "out" designate respectively the inlet and the outlet of the utility fluid flow chamber, "ncr" designates the number of cells per row of cells in the utility fluid flow chamber (in FIG. 1, ncr is equal to three for the chambers 27 and 28), and "nc" designates the last cell in the utility fluid flow chamber (in FIG. 1, in the chamber 27, nc designates L, nc-1 designates K, and nc-2 designates J, and in the chamber 28, nc designates A', nc-1 designates B', and nc-2 designates C').

The dynamic model also comprises a model for the behavior of the reagent(s) in the connection element 34 (FIG. 2) between the reagent feed means and the feed point 25a in cell 1, and a behavior model for the reactor medium in the connection element 35 between the outlet point 26 from cell 12 and the means for collecting the products of the reaction or a feed point or inlet to a cell in a second reaction chamber (not shown and constituting a second reaction block). It is important to take account of the connection elements 34 and 35 when making a dynamic model of the plate reactor since the total volume of these elements is not negligible compared with the volume of the reaction chamber 24, and can have an influence on the yield of the chemical reaction. Furthermore, in such connection elements, heat exchanges with the utility fluids are limited.

A plurality of plate reactor elements contribute to heat exchanges, such as the transition plates, 21, 22, the utility fluid flow chambers 27, 28, the adiabatic plates 20, 23, and the thermal environment of the reaction medium (presence of inserts in the reaction chamber 24).

Figure 4:
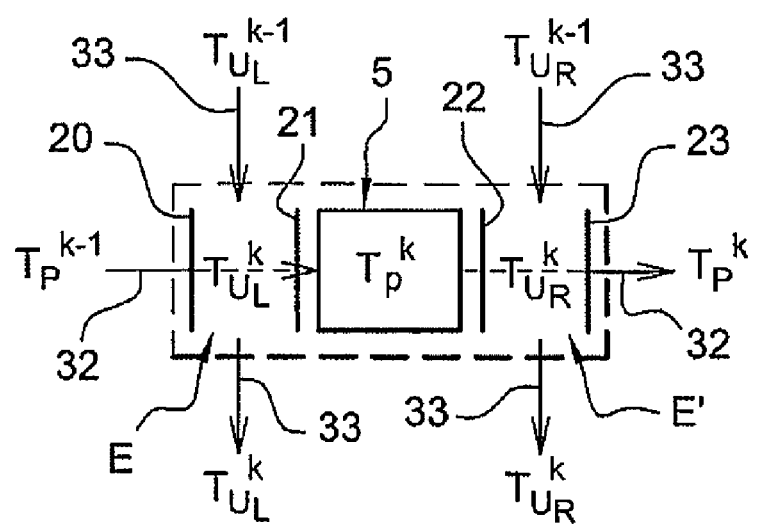
FIG. 4 is a diagrammatic view of an individual reaction cell associated with two individual utility fluid circulation cells.

The heat exchange model of the reactor medium in the individual reaction cells comprises characteristic equations applied to an individual reaction cell 5 represented diagrammatically in FIG. 4 by a rectangle which is defined by the two plates 21 and 22, and two utility fluid flow side cells E, E' defined respectively by the plates 20, 21 and 22, 23 in FIG. 1. The arrows 32 and 33 represent respectively the flow direction of the reaction medium in the individual cell 5 of the reaction chamber 24 and of the utility fluid in the individual side cells E, E' of the side chambers 27, 28, the flow direction of the utility fluid in the two chambers 27, 28 being a co-current flow relative to the flow of the reaction medium in the reaction chamber 24, contrary to that which is shown in FIG. 1.

The temperature of the utility fluid in an individual side cell depends on the temperature of the preceding individual side cell in the flow direction of the utility fluid, and also on the presence of utility zones in the reaction block. It is thus possible to represent all of the thermal configurations conceivable for the various flow directions of utility fluids relative to the reaction medium.

The subscripts $u_L$ and $u_R$ are used to designate the utility fluids respectively in the left chamber 27 and in the right chamber 28, with the other symbols having the same meanings as described above.

If it is assumed that the physical properties of the transition and adiabatic plates and of the utility fluid are constant for an individual cell at a given temperature, and that the temperature of each plate is calculated in the middle of the wall, the model for reaction medium heat exchanges comprises the following equations, for example:

the energy balance equation for the reaction medium in an individual reaction cell (in joules per second (J. s$^{-1}$)

$$\frac{d(u_p^k \times H_p^k)}{dt} = F_p^{k-1} H_p^{k-1} - F_p^k H_p^k + \Delta q_p^k \times V_p^k + h_{p,u_L}^k A_p^k (T_{u_L}^k - T_p^k) + h_{p,u_R}^k A_p^k (T_{u_R}^k - T_p^k)$$

with $$h_{p,u_L}^k = \frac{1}{\left(\frac{1}{h_{u_L}^k} + \frac{e_{pu_L}^k}{\lambda_{pu_L}^k} + \frac{1}{h_p^k}\right)},$$

$$h_{p,u_R}^k = \frac{1}{\left(\frac{1}{h_{u_R}^k} + \frac{e_{pu_R}^k}{\lambda_{pu_R}^k} + \frac{1}{h_p^k}\right)},$$

$$A_p^k = A^{cell} \times \frac{V_p^k}{V^{cell}}$$

and $$\Delta q_p^k = \sum_j (\Delta H r_j \times r_j^k)$$

with the heat balance equation for the utility fluid in the side cell of the left chamber 27 (in J.s$^{-1}$, with the same equation being used for the side cell in the right chamber 28):

$$\rho_{u_L}^k V_{u_L}^k C p_{u_L}^k \frac{dT_{u_L}^k}{dt} = F_{u_L}^k \rho_{u_L}^k C p_{u_L}^k (T_{u_L}^{k-1} - T_{u_L}^k) + h_{u_L,p}^k A_p^k (T_p^k - T_{u_L}^k)$$

the heat balance equation for the plate 21 disposed between an individual reaction cell and the side cell of the left chamber 27 (in J.s$^{-1}$, the same equation being used for the plate 22 disposed between an individual reaction cell and the side cell of the right chamber 28):

$$\rho_{pu_L}^k V_{pu_L}^k C p_{pu_L}^k \frac{dT_{pu_L}^k}{dt} = h_{pu_L,p}^k A_p^k (T_p^k - T_{pu_L}^k) + h_{pu_L,u_L}^k A^{cell} (T_{u_L}^k - T_{pu_L}^k)$$

with $$h_{pu_L,p}^k = \frac{1}{\left(\frac{e_{pu_L}^k}{2\lambda_{pu_L}^k} + \frac{1}{h_p^k}\right)} \text{ and } h_{pu_L,u_L}^k = \frac{1}{\left(\frac{e_{pu_L}^k}{2\lambda_{pu_L}^k} + \frac{1}{h_{u_L}^k}\right)}$$

in which $F_p$ and $F_u$ represent respectively the molar flow rate of the reaction medium in mol.s-1 and the volume flow rate of the utility fluid in m$^3$.s$^{-1}$, e is the thickness of the plates 21, 22 defining the reaction chamber 24 in m, $\lambda$ is the thermal conductivity in joules per second per meter per Kelvin (J.s$^{-1}$.m$^{-1}$.K$^{-1}$), h is the heat transfer coefficient in joules per second per square meter per Kelvin (J.s$^{-1}$.m$^{-2}$.K$^{-1}$), T is the temperature in K, Cp is the specific heat of the medium in joules per kilogram per kelvin (J.kg$^{-1}$.K$^{-1}$), $\rho$ is the density of the medium in kg.m$^{-3}$, $\Delta q$ is the heat generated by the reactions in J.m$^{-3}$s$^{-1}$, $\Delta$Hr is the molar heat of reaction in J.mol$^{-1}$, A is the area of heat exchange in m$^2$, and the subscripts pu$_L$ and pu$_R$ designate respectively the plate 21 between the reaction chamber 24 and the left chamber 27 and the plate 22 between the reaction chamber 24 and the right chamber 28.

The above-described model for heat exchange is extended to include the thermal inertia of the plate reactor. The thermal inertia model serves to take account of the structure and the composition of the various elements of the plate reactor. For example, it comprises the following equations, which differ from the preceding equations in that they take account of the thermal environment of the various fluids:

the energy balance equation for the environment of the reaction medium in an individual reaction cell (in J.s$^{-1}$):

$$\frac{d(u_p^k \times H_p^k)}{dt} = F_p^{f,k} H_p^{f,k} + F_p^{k-1} H_p^{k-1} - F_p^k H_p^k + \Delta q_p^k \times V_p^k + h_{p,pu_L}^k A_p^k (T_{pu_L}^k - T_p^k) + h_{p,pu_R}^k A_p^k (T_{pu_R}^k - T_p^k) + h_{p,te_p}^k A_p^k (T_{te_p}^k - T_p^k)$$

the heat balance equation for the utility fluid environment in the side cell of the left chamber 27 (in J.s$^{-1}$, with the same equation being used for the side cell in the right chamber 28):

$$\rho_{u_L}^k V_{u_L}^k C p_{u_L}^k \frac{dT_{u_L}^k}{dt} = F_{u_L}^k \rho_{u_L}^k C p_{u_L}^k (T_{u_L}^{k-1} - T_{u_L}^k) + h_{pu_L,u_L}^k A^{cell} (T_{pu_L}^k - T_{u_L}^k) + h_{u_L,te_{u_L}}^k A^{cell} (T_{te_{u_L}}^k - T_{u_L}^k)$$

the heat balance equation for the environment of the reaction medium in the individual reaction cell (in J.s$^{-1}$):

$$\rho_{te_p}^k V_{te_p}^k C p_{te_p}^k \frac{dT_{te_p}^k}{dt} = h_{p,te_p}^k A_p^k (T_p^k - T_{te_p}^k)$$

the heat balance equation for the environment of the adiabatic plate 20 of the left chamber 27 (in J.s$^{-1}$, the same equation being used for the adiabatic plate 23 of the right chamber 28):

$$\rho_{te_{u_L}}^k V_{te_{u_L}}^k C p_{te_{u_L}}^k \frac{dT_{te_{u_L}}^k}{dt} = h_{u_L,te_{u_L}}^k A_p^k (T_{u_L}^k - T_{te_{u_L}}^k)$$

in which the heat transfer coefficients are expressed as follows (in J.s$^{-1}$.m$^{-2}$.K$^{-1}$)

$$h_{p,pu_L}^k = \frac{1}{\frac{1}{h_p} + \frac{e_{p,pu_L}}{\lambda_{p,pu_L}}},$$

$$h_{p,te_p}^k = \frac{1}{\frac{1}{h_p} + \frac{e_{p,te_p}}{\lambda_{p,te_p}}},$$

$$h_{pu_L,u_L}^k = \frac{1}{\frac{1}{h_{u_L}} + \frac{e_{pu_L,u_L}}{\lambda_{pu_L,u_L}}} \text{ and}$$

$$h_{u_L,te_{u_L}}^k = \frac{1}{\frac{1}{h_{u_L}} + \frac{e_{u_L,te_{u_L}}}{\lambda_{u_L,te_{u_L}}}}$$

in which the subscripts $te_p$ and $te_u$ designate respectively the thermal environment of the reaction medium and of the utility medium, and $H^f$ is the molar enthalpy of the feed flow rate in J.mol$^{-1}$.

Heat exchanges between the reaction medium and the utility fluids are taken into account separately for each transition plate 21, 22 in order to include the thermal inertia due to these plates (e.g. made of stainless steel) in the dynamic model.

The heat balance equation for the environment of the reaction medium in the individual reaction cell, which depends on the temperature of the thermal environment of the reaction medium, makes it possible to take account of the thermal inertia due to the structure of the reaction chamber 24 and to the inserts (e.g. made of polyether-etherketone) present in said chamber. For a given individual cell, the heat transfer area and the mass of said thermal environment are calculated on the basis of the geometrical characteristics of the insert and on the basis of the structure of the reaction chamber 24.

The heat balance equations for the environment of the utility fluids in the individual cells of the left and right side chambers 27 and 28, which depend on the temperature of the thermal environment of the utility fluids, enable account to be taken of the thermal inertia due to the adiabatic plates 20 and 23 (e.g. of stainless steel) in the dynamic model. The characteristics of the thermal environment (heat transfer area, mass) are calculated from the geometrical characteristics of these adiabatic plates.

For a chemical reaction performed in a two-phase medium, the dynamic model of the reactor comprises all of the above-specified characteristic equations and balance equations (energy, heat, mass, etc.), established for each of the phases, the continuous phase being liquid, and the dispersed phase being a liquid or a gas. The dynamic models of the reaction medium in the reaction chamber 24, of the utility fluids in the side chambers 27 and 28, of the behavior of the reaction medium in the inlet and outlet elements 34 and 35 of the reaction chamber(s) 24, of the pressure drops, of the heat exchanges of the reaction medium in the individual cells 1 to 12, and of the thermal inertia of the reactor, are adapted to establish the dynamic model of an open reactor of the plate type for a reaction in a given two-phase medium.

To do this, the temperatures and the pressures in each of the phases are considered as being identical, and the reaction medium is assumed to be a pseudo-homogeneous medium with the physical properties of the corresponding two-phase medium being determined by association relationships associating the physical properties of the two-phase medium with the properties of each of its phases and also with their respective proportions, it being assumed that the phases are distributed homogeneously within each individual cell. Examples of association relationships are given below:

estimated density of the two-phase medium:

$$\frac{1}{\rho} = \sum_i \frac{n_i M_i}{m} \times \frac{1}{\rho_i}$$

estimated specific heat of the two-phase medium:

$$Cp = \frac{1}{m} \sum_i n_i M_i Cp_i$$

estimated thermal conductivity of the two-phase medium:

$$\lambda = \frac{1}{m} \sum_i n_i M_i \lambda_i$$

estimated viscosity of the two-phase medium:

$$\mu^{1/3} = \frac{1}{m} \sum_i n_i M_i \mu_i^{1/3}$$

in which $n_i$ represents the number of moles of the phase in mol, $M_i$ the molar mass of the phase in kilograms per mole (kg.mol$^{-1}$), m the total mass of the two-phase medium in kilograms (kg), i is a subscript specifying continuous or dispersed phase, $\lambda$ is the thermal conductivity of the medium in J.m$^{-1}$.s$^{-1}$.K$^{-1}$, and $\mu$ is the viscosity of the medium in pascal-seconds (Pa·s).

The precision of the dynamic model of the reactor for a reaction in a two-phase medium is based on the reaction medium being stable, and thus on there being equilibrium between the two phases. The equilibrium rules used in the mathematical model are a function of the size of the droplets of the dispersed phase in the continuous phase. The size and the distribution of the droplets are determined by means of a software tool for evaluating the droplet population.

The software tool for evaluating the population serves to predict how an initial distribution of droplet sizes will vary over time, and consequently to predict the Sauter diameter in the various individual reaction cells of the chamber 24 of the plate reactor. This variation depends on the rates at which droplets appear and disappear, which rates are directly associated with phenomena of coalescence and rupture. The phenomena of coalescence and rupture are introduced into the program from correlations relying on the physical and transport properties of the two-phase medium.

The matter transfer model relies on the assumption that the dispersed phase is present in the form of spherical droplets having a mean diameter equal to the Sauter diameter. Matter transfer between the two phases is modeled on the basis of Whitman's double-film theory.

In the dynamic model of the optimization method of the invention, the mass transfer characteristics are calculated for each individual reaction cell. Because of mass transfer correlations, all of the mass transfer characteristics (mass transfer coefficient, interface area, solubility) are associated with the physical properties of a liquid-liquid two-phase medium and with the Sauter diameter. Consequently, for a given liquid-liquid two-phase medium, a precise representation of the behavior of the plate reactor requires only a correct estimate for the Sauter diameter for each individual cell of the reaction chamber.

Figure 5A:
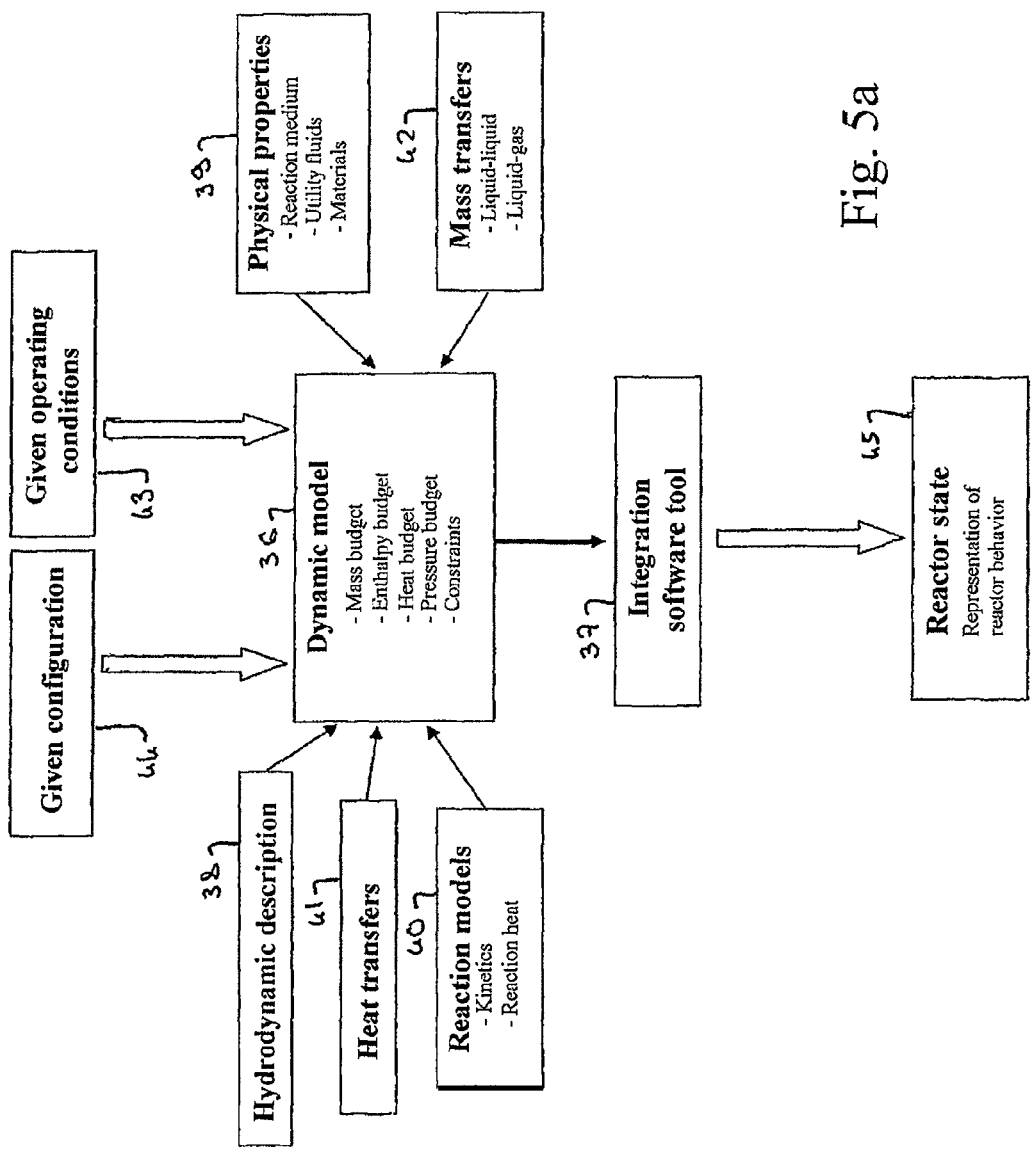
FIGS. 5a, 5b, and 5c are diagrams showing the main steps in the optimization method of the invention.

FIG. 5a is a diagram showing the essential steps in the optimization method of the invention, in which the dynamic model 36 of the plate reactor comprises a plurality of characteristic equations and balance equations for the reactor as described above.

An integration software tool 37 is used to simulate the behavior of the plate reactor on the basis of the dynamic model of the reactor for a given reaction. This tool enables the system of both algebraic and differential equations of the dynamic model to be solved by coupling with a database which includes the hydrodynamic description of the reactor 38, the physical properties 39 of the reaction medium, of the utility fluid(s), and of the materials of the components of the reactor (inserts, plates, . . .), models 40 for the reaction heat and kinetics of the chemical reaction, the heat transfers 41 between the various fluids, and the liquid-liquid matter transfers 42 or liquid-gas matter transfers 42 for reactions in a two-phase medium.

Numerous parameters or inputs involved in the various models are needed by the tool for integrating the dynamic model. These parameters comprise operating conditions 43 for the reaction such as the number of reactions, the number of reagents, the natures of the reagents, their flow rates, their temperature, their pressure, their feed duration, the characteristics of the reactions, the stoichometric coefficients, reaction orders, the pre-exponential factor for the rate constants, the activation energies, and the flow rates and the temperatures of the utility fluids, a description 44 of a basic configuration for the reactor comprising, for example, the number of individual cells per reaction block, the number of individual cells per row, the number of reaction blocks, the number of utility zones per reaction block, the dimensions of the plate reactor, the temperature of the outside medium, the heat exchange areas, the number of plates, their thicknesses, their densities, their heat capacities, their thermal conductivities, the dimensions of the inserts, their densities, their heat capacities, and the natures of the utility fluids, and other integration parameters such as tolerances on absolute errors or the time available for integration.

The person skilled in the art is aware of this kind of tool and database. The database is for example Bipphy®. The integration software tool is for example DISCo, which is capable of solving dynamic models with more than 5000 characteristic and balance equations with great speed and accuracy.

DISCo (Do Integrate by Software Components) is a tool for integrating systems of algebraic and differential equations based on Gear's method of backward differentiation using a predictor-corrector scheme. This tool presents numerous advantages such as processing the system as a whole, without discriminating between equations or variables, the possibility of integrating additional equations and thus additional variables into the basic system, thereby providing great flexibility to the mathematical model, automatic procedures for detecting events, and for calculating consistent initial conditions, which is particularly useful when looking for and managing events (starting procedure, dynamics), and the possibility of processing the system by means a sparse matrix which leads to a major reduction in computation time.

The integration software tool 37 serves to simulate the behavior of the chemical reactor referred to as the "reactor state" 45 for a given chemical reaction. By way of example, this simulation makes it possible to predict the yield of the chemical reaction, temperature changes during the reaction, etc.

Figure 5B:
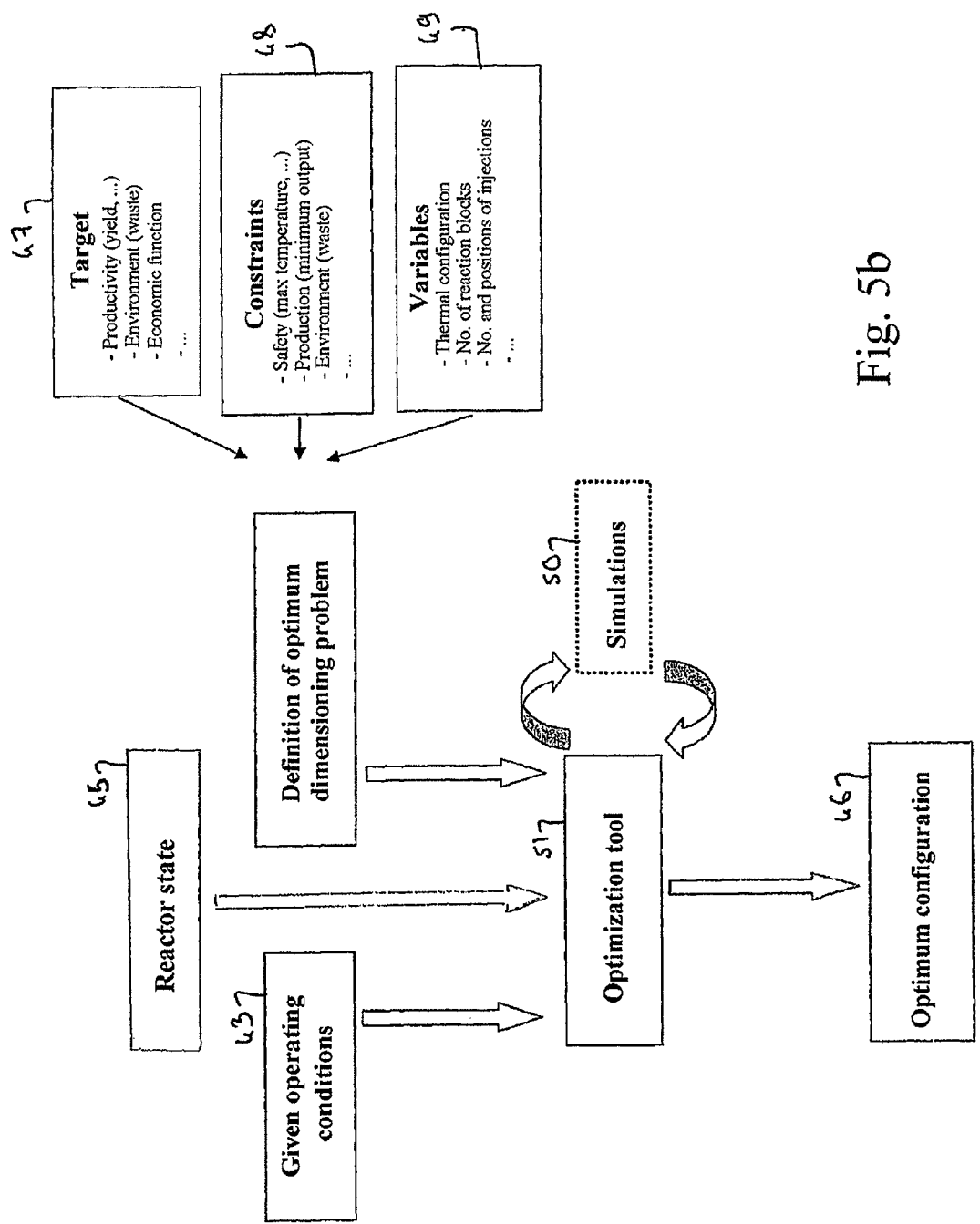

In FIG. 5b, the operator is seeking initially to define an optimum size or configuration for the reactor 46. To do this, the operator determines or evaluates the target(s) 47 that are to be achieved, such as improving productivity (reaction yield), being environmentally friendly (small quantities of waste), or low in cost, sets the constraints 48 that are to be complied with and which may relate, for example, to safety, e.g. giving a maximum temperature for the reaction medium that is not to be exceeded, or to productivity or profitability with predetermined maximum or minimum quantities of reagents, or to the environment, with limits on waste that is toxic or harmful or difficult to recycle or to biodegrade, and also sets the variable characteristics 49 in the structure of the reactor.

These variable characteristics 49 comprise, for example, the number of reaction blocks, the number of utility zones per block, the number and positions of the feed points, the dimensions of the reaction chambers, the co-current, counter-current, or crossed-current flow directions of the utility fluid relative to the flow of the reaction medium in the reaction chamber, and the number, natures, and geometries of the inserts in the reaction chamber.

In a variant, the target to be achieved could be a mathematical function comprising a plurality of quantitative criteria. For example, the function giving the target for a production line may be defined relative to a productivity criterion and an environmental criterion by the following equation:

$$f = q_p \times k_p - q_x \times k_x$$

where $q_p$ is the quantity of product looked for from the reaction, $k_p$ is the unit cost of the product, $q_x$ is the quantity of reaction product that is of no value, and $k_x$ is the cost of processing or eliminating this product.

The operator can also define acceptable variations for these targets and the constraints, i.e. the margins that are authorized.

The method of the invention makes it possible to optimize 46 the dimensions or the configuration of the reactor from the above-defined reactor state 45, the above-specified operating conditions 43, and said targets 47, constraints 48, and variables 49. Optimization is obtained by performing a plurality of successive simulations 50 which enable the greatest possible number of targets or target functions to be achieved while satisfying the constraints, and possibly also the authorized margins for the targets and for the constraints, by acting on all of the variable characteristics of the structure of the plate reactor.

The dimensions of the reaction are optimized by means of a second software tool 51, such as SQP® (Successive Quadratic Programming) which makes it possible to define 46 the optimum parameters for dimensioning or configuring the reactor for a given reaction.

Figure 5C:
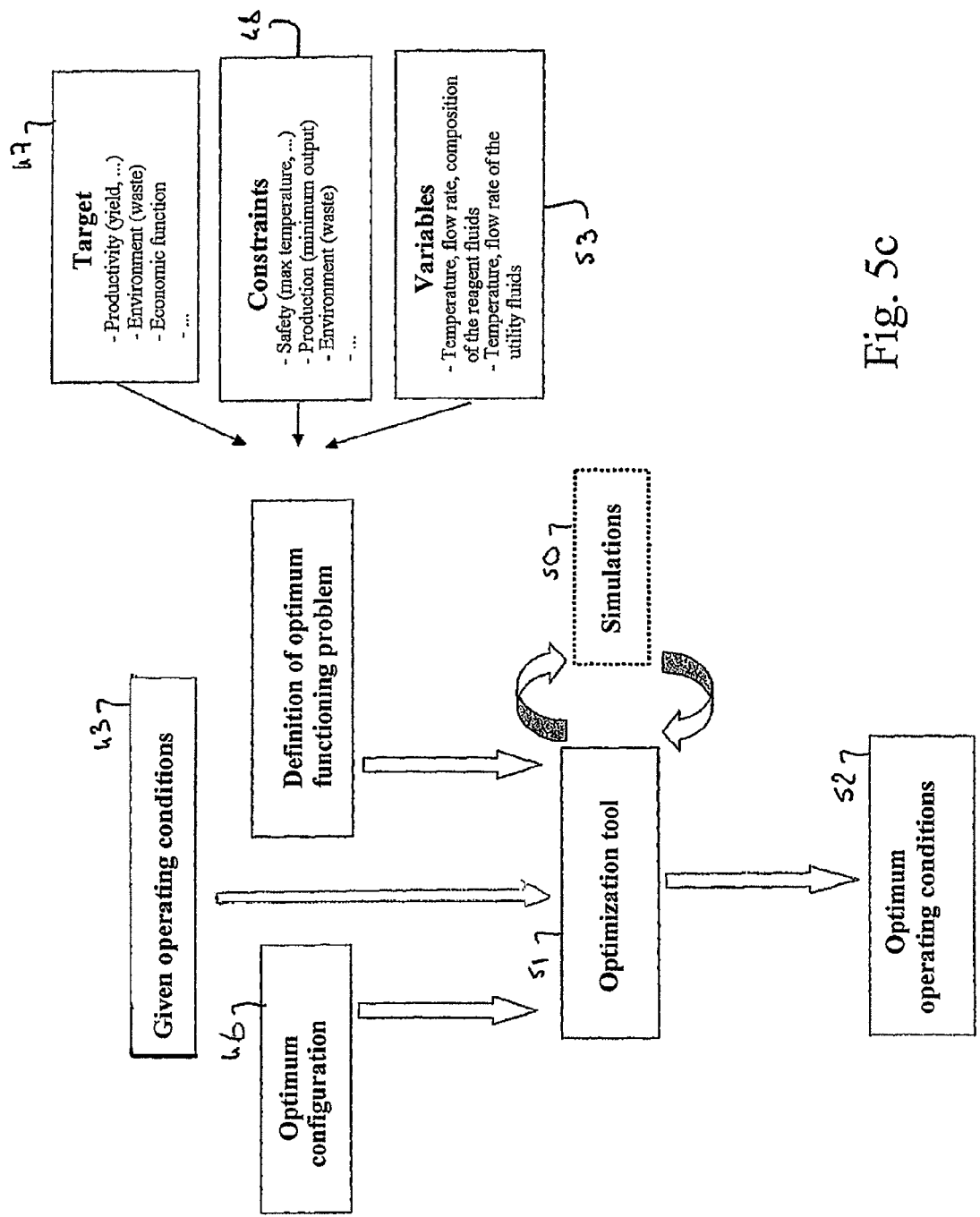

In FIG. 5c, the operator then seeks to determine the optimum operating conditions 52 for optimizing the operation of the reactor for the given reaction. The target(s) 47 to be achieved and the constraints 48 to be complied with remain the same as while optimizing the dimensions of the reactor. Only the variables change, which are the reaction variables 53 which comprise for example the flow rate, the temperature, the pressure, and the composition of the various reagents, the order in which the reagents are fed into the reaction chamber 24, and the flow rates and the temperatures of the utility fluids.

The method of the invention makes it possible to optimize the operation of the reactor by determining optimum operating conditions for the reactor for a given reaction, on the basis of the previously-defined optimum dimensioning or size for the reactor, the above-mentioned operating conditions, and the above-mentioned targets, constraints, and variables. Optimization is obtained by performing a plurality of successive simulations 50 which makes it possible to achieve as many as possible of the targets or target functions mentioned above while complying with the constraints, and possibly also the authorized margins for the targets and for the constraints, and by acting on all of the variable data for the reaction.

The operation of the reactor is also optimized by means of the above-mentioned software tool 51. Optimum operating conditions make it possible, for example, to perform comparative studies in terms of reactor control, safety, and sensitivity of the chemical reaction.

Examples of optimizing the behavior of a plate reactor of a given size and for given reactions are illustrated in FIGS. 6 to 12.

Figure 6:
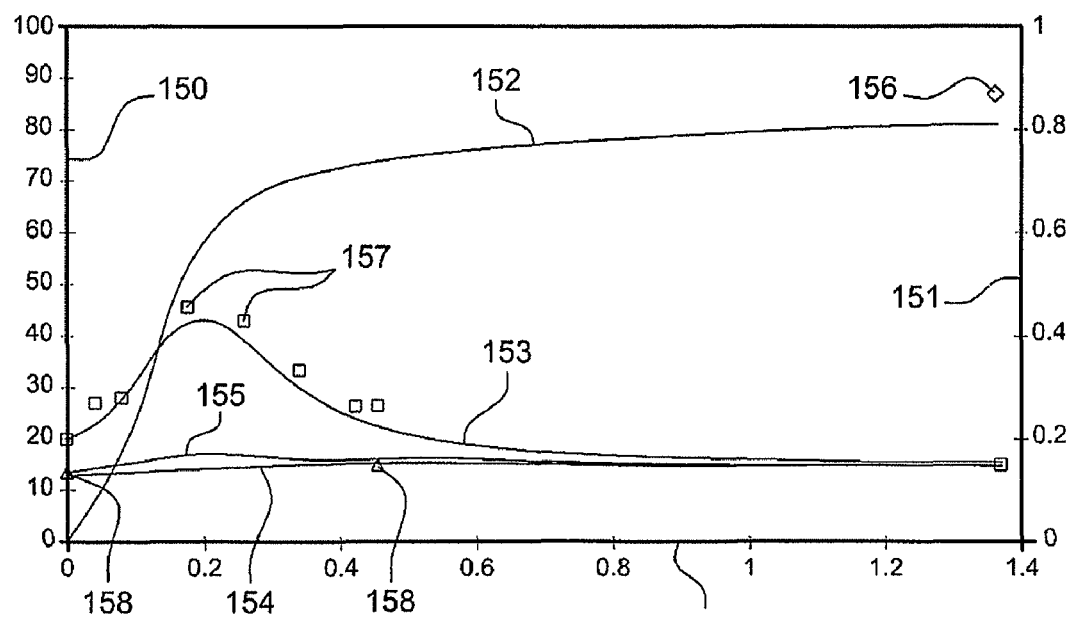
FIGS. 6 and 7 are graphs showing the influences of reagent concentration and flow rate, and of utility fluid flow rate on the temperature and the yield of the sodium thiosulfate oxidation reaction.
Figure 7:
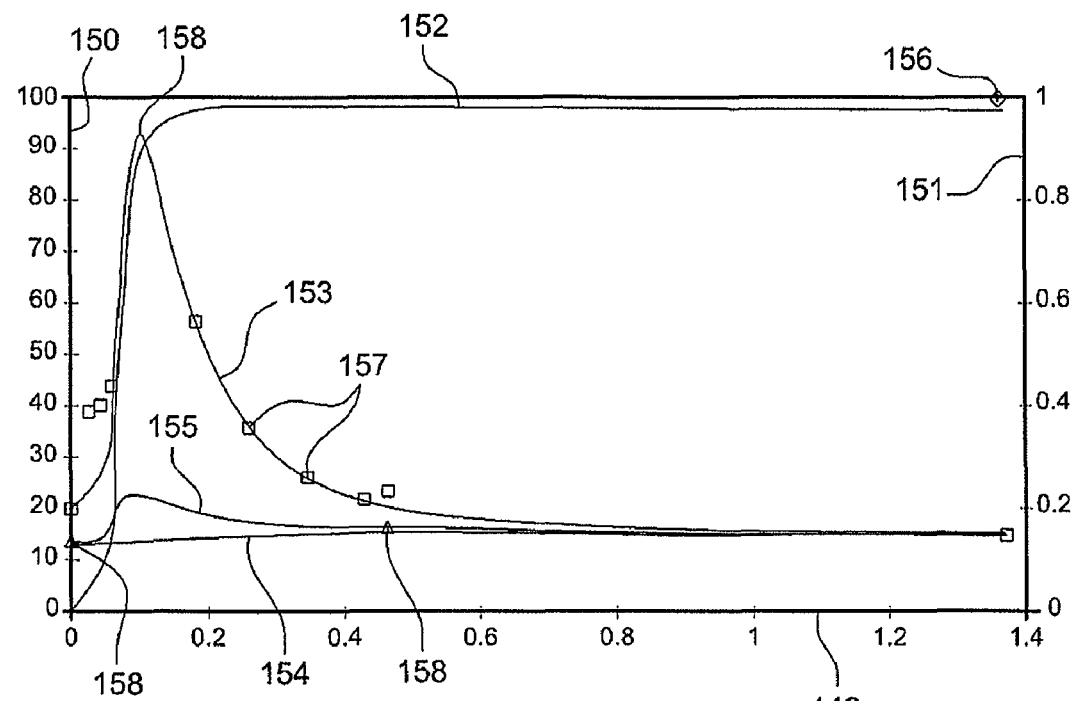

FIGS. 6 and 7 are graphs tracking the reaction of oxidizing sodium thiosulfate. The abscissa axis 149 represents the volume of the reaction chamber in liters. The ordinate axis 150 on the left shows temperature in degrees Celsius, and the ordinate axis 151 on the right gives the yield of the reaction on a scale up to 1.

Curve 152 shows how the yield of the oxidation reaction varies, curves 153, 154, and 155 showing variations in the temperatures of the reaction medium, of the utility fluids, and of the plates defining the reaction chamber respectively.

Sodium thiosulfate is oxidized by hydrogen peroxide using the following reaction, with the reaction products being sodium trithionate, sodium sulfate, and water.

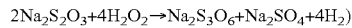

$$2Na_2S_2O_3 + 4H_2O_2 \rightarrow Na_2S_3O_6 + Na_2SO_4 + 4H_2)$$

The reaction is highly exothermic and takes place in a homogeneous liquid medium in a plate reactor having three reaction blocks. The above-mentioned experimental studies of resident time distribution make it possible to treat the plate reactor as a succession of 91 individual cells, the reactor comprising three reaction blocks each containing 27 individual cells, and a transition element containing 10 individual cells between two reaction blocks. The number of equations in the dynamic model of the reactor for this reaction is 1920.

In FIG. 6, the reaction medium has a low concentration of reagents, with the sodium thiosulfate being injected at 40 liters per hour (L.h$^{-1}$) at a concentration of 0.62 moles per liter (mol.L$^{-1}$), the hydrogen peroxide at 10 L.h$^{-1}$ with a concentration of 1.28 mol.L$^{-1}$, and the utility fluids were water at 14° C. fed at a flow rate of 3.4 m$^3$.h$^{-1}$ in each reaction block.

The operator set a single target, i.e. improving the yield of the optimization reaction, a reaction variable datum, which was the flow rate of the utility fluids, and a temperature constraint on the reaction medium which must remain below 45° C.

In FIG. 7, the reaction medium has a higher concentration of reagent, the sodium thiosulfate being injected at 40 L.h$^{-1}$ at a concentration of 0.75 mol.L$^{-1}$, the hydrogen peroxide at 10 L.h$^{-1}$ with a concentration of 1.59 mol.L$^{-1}$, and the utility fluids being water at 14° C. fed at a flow rate of 1.8 m$^3$.h$^{-1}$ in the first reaction block and of 0.9 m$^3$.h$^{-1}$ in the two others reaction blocks.

The method of the invention makes it possible to optimize the plate reactor for the sodium thiosulfate oxidation reaction by acting on reaction variable data such as the utility fluids flow rates.

The reaction of oxidizing sodium thiosulfate is then executed in a plate reactor built for operating with the optimized flow rates of the utility fluids, and measurements of physical parameters such as the temperature and the pressure are done during this execution for validating the operation of the reactor.

In FIGS. 6 and 7, the lozenge-shaped points 156 are experimental measurements of the yield for the reaction, the square points 157 and the triangular points 158 are respective experimental measurements of the temperature of the reaction medium and of the utility fluids.

The experimental results are close to the corresponding curves, thus validating the simulation of this chemical reaction in the plate reactor, and thus enabling the precision of the dynamic model to be evaluated.

The simulation further serves to locate accurately the temperature peak 158 in FIG. 7 (at more than 90° C.) which does not appear in the experimental measurements because of the small number of sensors and how they are disposed, the highest measured reaction being less than 60° C.

Figure 8:
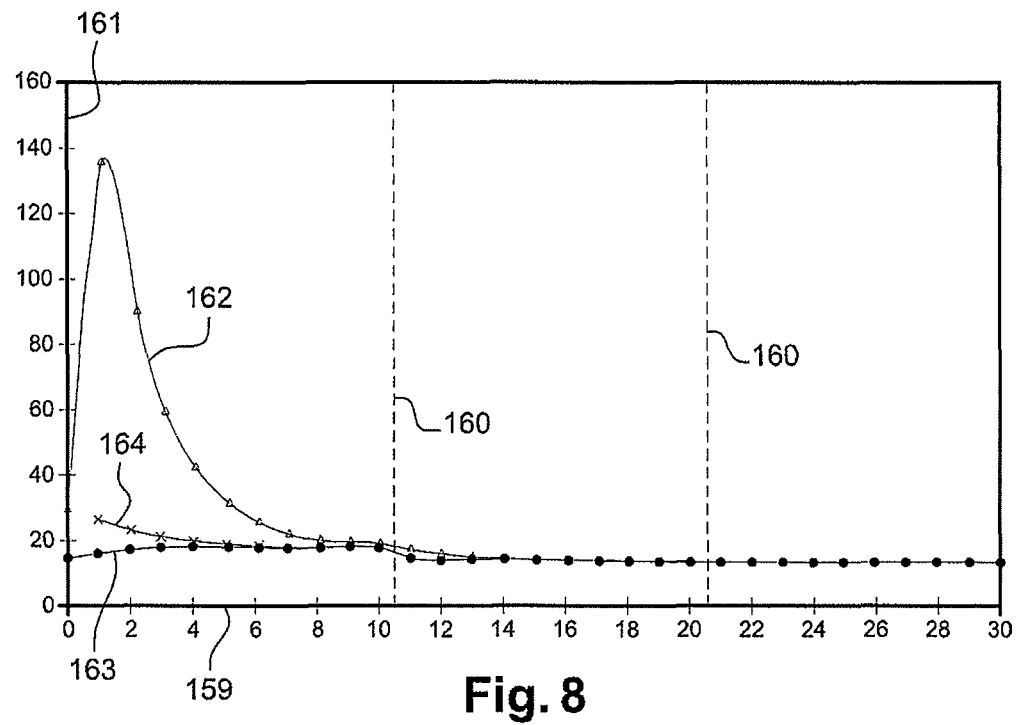
FIGS. 8 to 10 are graphs showing the influences of the number and the disposition of the reagent feed points on the temperature of the acetic anhydride hydrolysis reaction.
Figure 9:
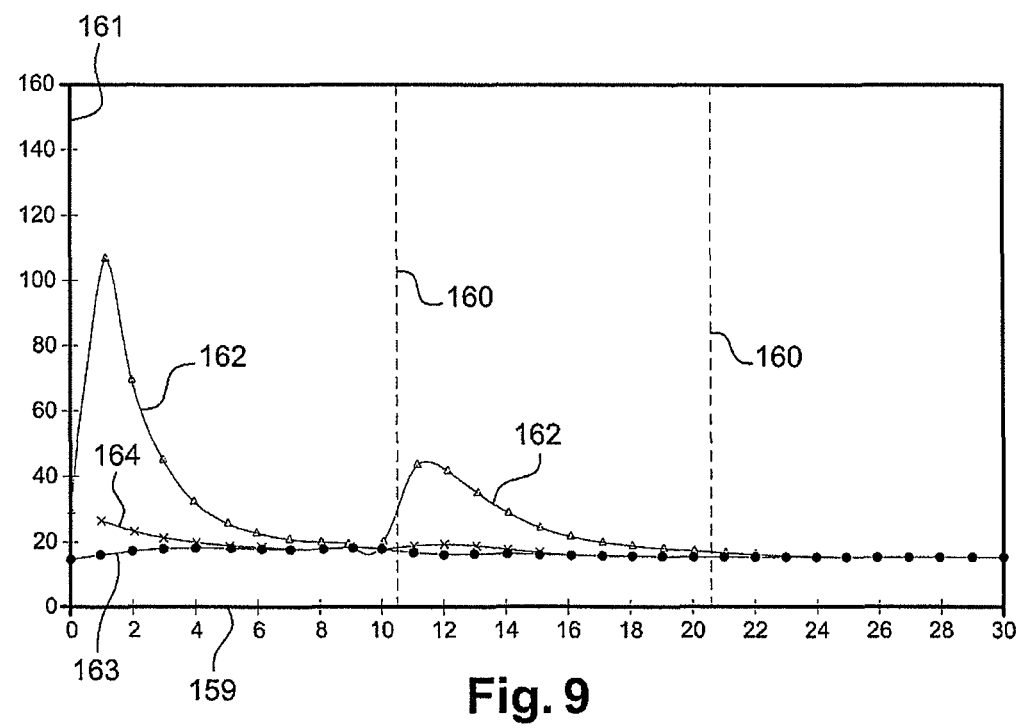
Figure 10:
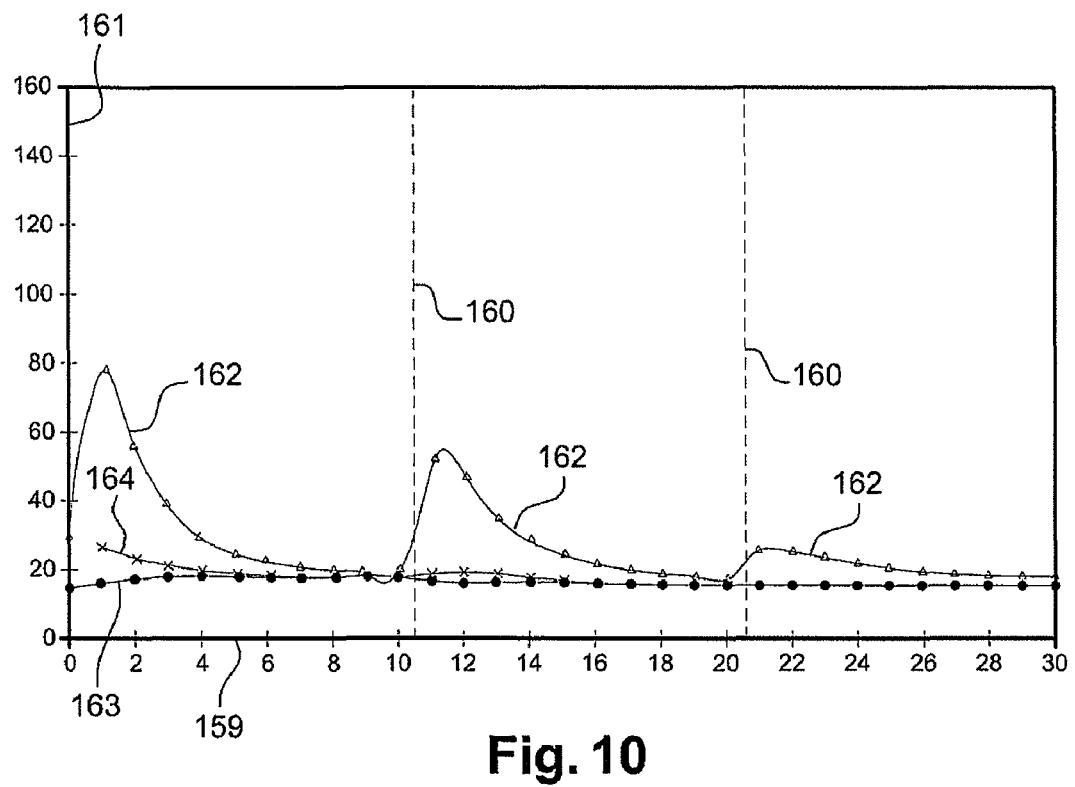

FIGS. 8 to 10 are graphs tracking the reaction of hydrolyzing acetic anhydride. The abscissa axis 159 represents the numbers of the individual reaction cells. In this embodiment, the plate reactor had thirty individual cells subdivided into three reaction blocks, the passage from one reaction chamber to a following block being represented diagrammatically by the vertical dashed lines 160. The ordinate axis 161 represents temperature in degrees Celsius. The curves 162, 163, and 164 show variations in the temperatures of the reaction medium, of the utility fluids, and of the transition plates defining the reaction chamber, respectively.

The hydrolysis of acetic anhydride produces acetic acid via the following reaction:

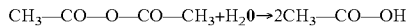

$$CH_3-CO-O-CO-CH_3 + H_2O \rightarrow 2CH_3-CO-OH$$

The operator set a target of maximum productivity, a temperature constraint on the reaction medium which was to remain less than 80° C., and reactor structure variable characteristics which were the number and the disposition of reaction feed points for optimizing the dimensioning of the reactor.

In FIG. 8, the acetic anhydride was injected entirely into cell 1 of the reaction chamber at a temperature of 30° C. and at a rate of 40 L.h$^{-1}$. Water was also injected into cell 1 at a temperature of 30° C. and at a rate of 10 L.h$^{-1}$. The utility fluids were at a temperature of 15° C. and at a flow rate of 10,800 L.h$^{-1}$ since the reaction is highly exothermic. It can be seen that the values selected for the optimization variables do not enable the temperature constraint to be complied with.

In FIG. 9, the acetic anhydride was injected entirely into cell 1 of the reaction chamber at a temperature of 30° C. and at a rate of 40 L.h$^{-1}$. Water was injected into cell 1 (first cell of the first block) at a temperature of 30° C. and at a rate of 5 L.h$^{-1}$, and into cell 11 (first cell of the second reaction block), at a temperature of 30° C. and at a rate of 5 L.h$^{-1}$. The utility fluids were at a temperature of 15° C. and at a flow rate of 10,800 L.h$^{-1}$.

Water was thus introduced into the reaction chamber twice, at two different feed points. This made it possible to reduce a little the maximum temperature of the reaction medium, which went from 138° C. in FIG. 8 to 104° C. in FIG. 9. The number and the disposition of the reagent feed points in the reactor were nevertheless not correct since the temperature constraint was still not complied with.

In FIG. 10, the acetic anhydride was injected entirely into cell 1 of the reaction chamber at a temperature of 30° C. and at a flow rate of 40 L.h$^{-1}$. Water was injected into the cell 1 at a temperature of 30° C. and at a flow rate of 3.33 L.h$^{-1}$, into cell 11 at a temperature of 30° C. and at a flow rate of 3.33 L.h$^{-1}$, and into cell 21 (the first cell of the first block) at a temperature of 30° C. and at a flow rate of 3.33 L.h$^{-1}$. The utility fluids were at a temperature of 15° C. and at a flow rate of 10,800 L.h$^{-1}$.

In this case, water was introduced into the reaction chamber three times over at three different feed points. This made it possible to reduce the maximum temperature of the reaction medium to below the constraint of 80° C. The optimization method thus made it possible to identify appropriate dimensioning that satisfies the productivity target and that complies with the temperature constraint.

Figure 11:
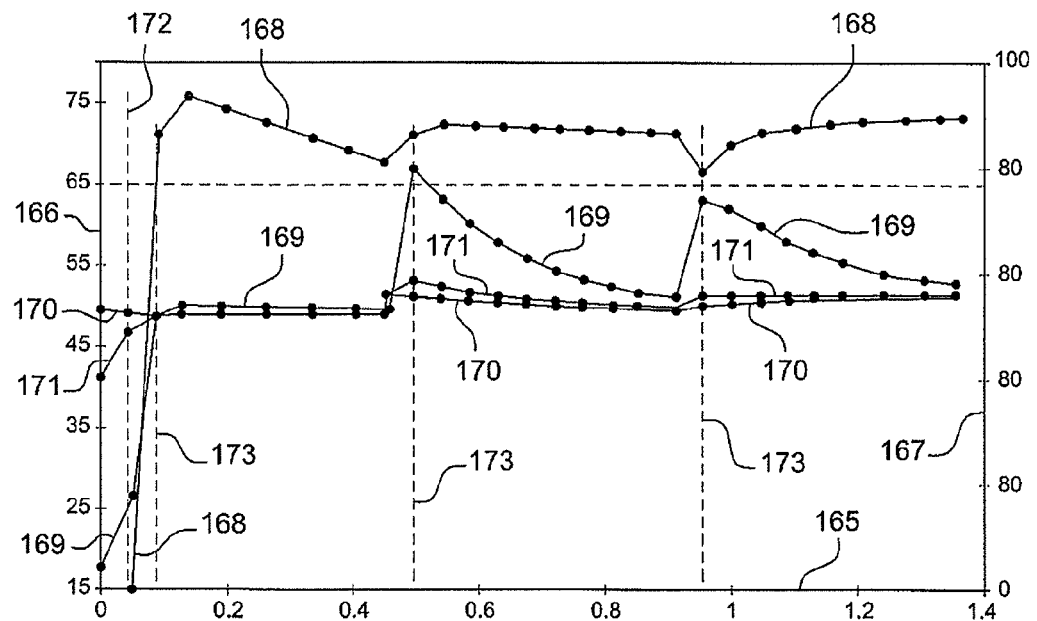
FIGS. 11 and 12 are graphs showing the influences of the reagent feed rate at a plurality of feed points on the temperature and the yield of the reaction for producing neopentyl glycol.
Figure 12:
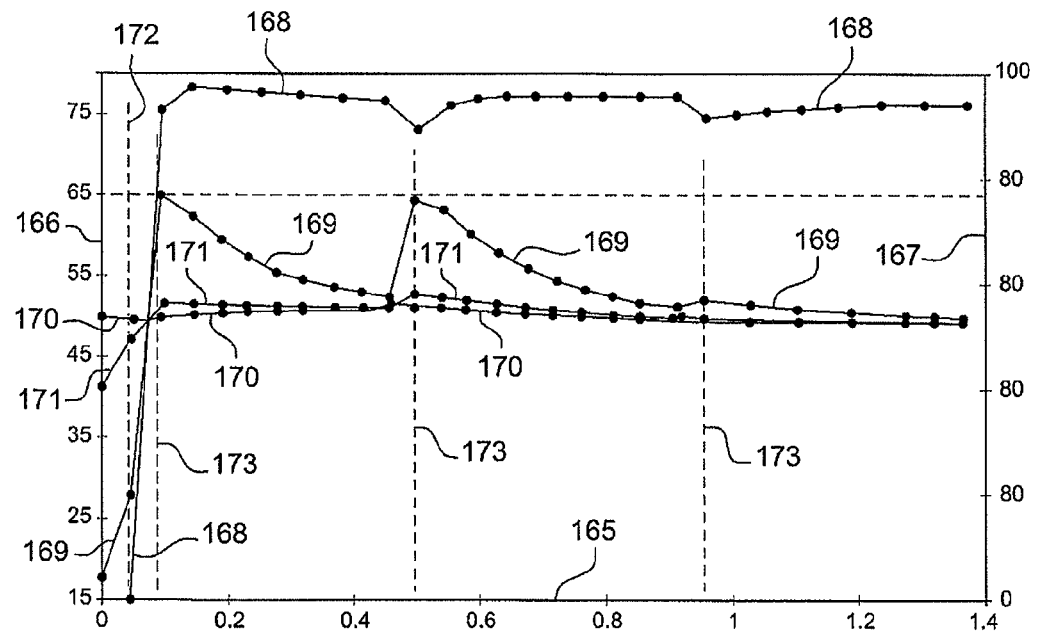

FIGS. 11 and 12 are graphs tracking the reaction of producing neopentyl glycol. The abscissa axis 165 represents the volume of the reaction chamber in liters. In this implementation, the reaction chamber comprised 40 individual cells subdivided into four blocks of 10 individual cells each having a volume of about 0.035 liters (L). The left-hand ordinate axis 166 represents temperature in degree Celsius, and the right-hand ordinate axis 167 represents the yield of the reaction in percentage.

Curve 168 shows how the yield of the reaction varies, while curves 169, 170, and 171 show respectively variation in the temperature of the reaction medium, of the utility fluids, and of the plates defining the reaction chamber.

The equation for producing neopentyl glycol is as follows:

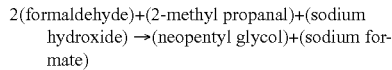

2(formaldehyde)+(2-methyl propanal)+(sodium hydroxide) →(neopentyl glycol)+(sodium formate)

In FIGS. 11 and 12, the vertical dashed lines 172 and 173 represent respectively the sodium hydroxide feed point and the 2-methyl propanal feed point. The sodium hydroxide was thus introduced once only when the volume of the reaction chamber was close to 0.05 L, which corresponds to the second cell in the reaction chamber (0.035 L per individual cell), and the 2-methyl propanal was introduced on three occasions, into the third cell, the fifteenth cell, and the twenty-eighth cell.

In FIG. 11, given that the reaction is exothermic, the utility fluids were at a temperature of 50° C. and at a flow rate of 1.5 m$^3$.h$^{-1}$. The reagents were injected at a temperature of 18° C. and the 2-methyl propanal at a concentration of 2 mol.kg$^{-1}$ for a total flow rate of 9.14 L.h$^{-1}$ (three injections at identical flow rats of about 3.05 L.h$^{-1}$). The conversion ratio achieved was 89.4% and the maximum temperature of the reaction medium during the reaction was 66.6° C.

The operator set a target of increasing yield from the reaction producing neopentyl glycol, the variable data for optimizing the operation of the reaction, which were the feed rates of 2-methyl propanal for each feed point, and a constraint to be complied with, which was the maximum temperature of the reaction medium which was not to exceed 65° C.

The result is shown in FIG. 12, where the utility fluids are at a temperature of 50° C. and a flow rate of 1.5 m$^3$.h$^{-1}$, the reagents are fed at a temperature of 18° C. and the 2-methyl propanal at a concentration of 2 mol.kg$^{-1}$ for a total flow rate of 9.14 L.h$^{-1}$. The three injections of 2-methyl propanal are at different flow rates; 5.91 L.h$^{-1}$ for the first feed to cell 3, 2.73 L.h$^{-1}$ for the second feed to cell 11, and 0.50 L.h$^{-1}$ for the third feed to cell 21. The conversion ratio achieved is 95.6% and the maximum temperature of the reaction medium during the reaction reached 65° C., thereby complying with the imposed constraint.

The optimization method thus makes it possible to achieve a target yield for a reaction while complying with a temperature constraint by acting on a reaction variable data which in this case are the feed rates of a reagent at a plurality of points into the reaction chamber.

The invention claimed is:

1. A method of optimizing a chemical reaction in a reactor, comprising:
   a) defining mass balance equations, energy balance equations, and constraint equations of a dynamic model of the reactor for a given reaction on the basis of a model of the reaction chamber and of the heat exchanges between said reaction chamber and the side chambers for circulating utility fluid;
   b) simulating the behavior of the reactor for said reaction by applying an integration software tool to solve the above equations of the dynamic model using theoretical values of physical parameters in the dynamic model;
   c) varying at least dimension parameters of the reactor and selecting optimal dimension parameters for which evaluating targets are achieved and constraints are complied with;
   d) building a plate reactor by at least stacking plates defining said at least one block according to the optimal dimension parameters;
   e) using the built plate reactor constituted by a stack of plates defining between them at least one block having a reaction chamber formed between two heat exchange side chambers for circulating a heat exchange utility fluid, means for feeding the reaction chamber with a continuous flow of one or more reagents, and means for feeding the two side chambers with a continuous flow of utility fluid built in step d); and
   f) measuring physical parameters of said reaction including the temperature and the pressure during the execution of said reaction in the built plate reactor, and validating operation of the built plate reactor if said measurements are close to the theoretical values of physical parameters;
   g) establishing a new dynamic model of the reactor on the basis of the built reactor; h) applying the integration software tool to this new dynamic model to solve the above equations;
   i) optimizing again the said set of dimension and/or operation parameters of the reactor; and
   j) modifying if necessary the said built reactor, accordingly to the new optimized set of parameters.

2. A method according to claim 1, wherein the model of the reaction chamber includes subdividing the chamber into a series of successive individual cells each containing a thoroughly stirred fluid medium.

3. A method according to claim 2, wherein the fluid medium in each individual cell is homogeneous and its state and its variations are defined by mass balance, energy balance, pressure balance, and volume constraint equations.

4. A method according to claim 2, wherein the fluid medium contained in each individual cell of the reaction chamber is a two-phase medium comprising a continuous phase and a dispersed phase.

5. A method according to claim 4, wherein the state and the variation of the two-phase medium are defined in each individual cell from equations estimating the density, the specific heat, the thermal conductivity, and the viscosity of the two-phase medium, and from mass balance, energy balance, pressure balance, and volume constraint equations.

6. A method according to claim 4, wherein the two-phase reaction medium is a pseudo-homogeneous medium and the physical properties of the two phases are determined by association relationships associating the physical properties of the two-phase medium with the properties of each of the phases and also their proportions.

7. A method according to claim 6, comprising applying to the phase mixture rules for equilibrium between the two phases at a function of the size of the droplets of the dispersed phase, of the thermodynamic properties of the phases present, and/or of the flow conditions.

8. A method according to claim 6 comprising following variation in the size of the droplets of the dispersed phase in the individual cells of the reaction chamber(s).

9. A method according to claim 2, wherein the heat exchange model includes subdividing each of the side chambers into a series of individual cells each containing a thoroughly stirred fluid medium, the number of individual cells in each side chamber being equal to the number of individual cells in the reaction chamber, and in defining a flow direction for the utility fluid in each individual cell relative to the flow direction of the reaction fluid in the corresponding individual cell of the reaction chamber.

10. A method according to claim 9, wherein the heat exchange model also includes heat balance equations relating to the reaction fluid, to the plates defining the heat exchange side chambers, and to the utility fluids circulating in the side chambers, and mass balance equations for the utility fluids in the above-specified individual cells of the side chambers.

11. A method according to claim 2, comprising modeling the hydrodynamic behavior of the reactor on the basis of experimental studies of the resident time distribution of the fluids in the portions of the reactor in order to define the number of individual cells having content that is thoroughly stirred.

12. A method according to claim 2, wherein the dynamic model of the reactor also comprises a model of the reaction based on equations for reaction rate, rate of production of the constituents of the reaction, and rate of generation of heat, in each individual cell of the reaction chamber(s).

13. A method according to claim 2, comprising optimizing the dimensioning of the reactor for given targets and constraints by adjusting parameters such as the number of series of individual cells, the number of reagent feed points into the reaction chamber, the flow direction of the utility fluid relative to the reaction medium, the nature and the distribution of the utility fluid, the volume of the reaction chamber, and/or the volumes of the side chambers for circulating utility fluid.

14. A method according to claim 13 also including defining limit values for operating parameters that satisfy safety and/or environmental constraints.

15. A method according to claim 1, wherein the dynamic model of the reactor also includes models for inlet and outlet zones of the reactor, inlet and outlet zones for each reaction chamber, and transition zones between the blocks of the reactor.

16. A method according to claim 1, wherein the dynamic model of the reactor also includes modeling matter transfer in a two-phase reaction medium between the two phases of the reaction medium on the basis of the physical properties of the two-phase medium and on the basis of the size of the droplets of the dispersed phase.

17. A method according to claim 1, wherein the dynamic model of the reactor also includes a model of heat transfer based on definitions of heat transfer coefficients between the plates defining the side chambers and the fluids flowing in the reaction chamber and the side chambers, and estimates of the film coefficients of the reaction fluid and of the utility fluid.

18. A method according to claim 1, wherein the dynamic model of the reactor also includes a model of reaction fluid pressure drops in the reactor based on experimental measurements.

19. A method according to claim 1, wherein the method also includes an estimate of the physical properties of the components of the reactor and of the reaction and utility fluids.

20. A method according to claim 1, comprising optimizing the operation of the reactor for given targets and constraints by adjusting operating parameters comprising temperatures, pressures, compositions, and/or flow rates of the reaction fluids and of the utility fluids.

21. A method according to claim 20, wherein, for a reactor or reaction chamber including a plurality of fluid inlet zones, the method includes adjusting the flow rates, the temperatures, the pressures, and/or the compositions of the fluids injected into these various zones.

* * * * *

UNITED STATES PATENT AND TRADEMARK OFFICE
CERTIFICATE OF CORRECTION

PATENT NO. : 8,065,038 B2
APPLICATION NO. : 11/773667
DATED : November 22, 2011
INVENTOR(S) : Elgue et al.

It is certified that error appears in the above-identified patent and that said Letters Patent is hereby corrected as shown below:

Column 17
Line 31, "$2Na_2S_2O_3 + 4H_2O_2 \rightarrow Na_2S_3O_6 + Na_2SO_4 + 4H_2$)"
should read --$2Na_2S_2O_3 + 4H_2O_2 \rightarrow Na_2S_3O_6 + Na_2SO_4 + 4H_2O$--.

Signed and Sealed this
First Day of May, 2012

David J. Kappos
*Director of the United States Patent and Trademark Office*